(12) United States Patent
Klapproth et al.

(10) Patent No.: US 7,390,649 B2
(45) Date of Patent: Jun. 24, 2008

(54) SENSOR CHIPS WITH MULTIPLE LAYERS OF POLYSILOXANE

(75) Inventors: Holger Klapproth, Freiburg (DE); Jürgen Rühe, Eichstetten (DE); Sonia Mohry, Freiburg (DE)

(73) Assignee: Micronas Holding GmbH, Freiburg (DE)

( * ) Notice: Subject to any disclaimer, the term of this patent is extended or adjusted under 35 U.S.C. 154(b) by 0 days.

(21) Appl. No.: 10/343,024

(22) PCT Filed: Jul. 24, 2001

(86) PCT No.: PCT/EP01/08545

§ 371 (c)(1),
(2), (4) Date: May 5, 2003

(87) PCT Pub. No.: WO02/10752

PCT Pub. Date: Feb. 7, 2002

(65) Prior Publication Data

US 2004/0081835 A1    Apr. 29, 2004

(30) Foreign Application Priority Data

Jul. 27, 2000  (EP) ................................. 00116342

(51) Int. Cl.
*C12M 1/34* (2006.01)
(52) U.S. Cl. .................... 435/287.1; 427/2.11; 427/2.13; 427/387; 428/446; 428/447; 428/448; 435/6; 435/7.1; 436/527
(58) Field of Classification Search ................ 427/387; 428/447, 426, 446, 702; 106/287.13, 287.16
See application file for complete search history.

(56) References Cited

U.S. PATENT DOCUMENTS

| 5,182,143 | A | * | 1/1993 | Holmes-Farley et al. ..... 427/409 |
| 5,525,264 | A | * | 6/1996 | Cronin et al. ................ 252/583 |
| 5,567,235 | A | * | 10/1996 | Carson et al. .......... 106/287.16 |
| 5,619,288 | A | * | 4/1997 | White et al. ................. 351/159 |
| 5,661,092 | A |   | 8/1997 | Koberstein et al. |
| 5,667,928 | A |   | 9/1997 | Thomas et al. |
| 5,696,314 | A |   | 12/1997 | McCaffrey et al. |
| 5,919,523 | A | * | 7/1999 | Sundberg et al. ............. 427/333 |
| 5,999,781 | A | * | 12/1999 | Gervasi et al. .............. 399/266 |
| 6,013,855 | A | * | 1/2000 | McPherson et al. ...... 623/23.76 |
| 6,732,583 | B1 | * | 5/2004 | Yasuda et al. ............ 73/204.26 |
| 2002/0006632 | A1 | * | 1/2002 | Ponnampalam et al. .... 435/7.92 |
| 2003/0153069 | A1 | * | 8/2003 | Seo et al. ................. 435/287.2 |

FOREIGN PATENT DOCUMENTS

WO    WO 98/31839    7/1998

OTHER PUBLICATIONS

G.T. Hermanson; Bioconjugate Techniques; 1996; pp. 137-166, Academic Press.
www.sigmaaldrich.com/catalog/search/ProductDetail/SIGMA/G1535, last downloaded on Jun. 10, 2005, 2 pages.
Linda A Chrisey et al., Covalent Attachment of Synthetic DNA to Self-assembled Monolayer Films, Nucleic Acids Research, 1996, pp. 3031-3039, vol. 24, No. 15.
Webster's New Collegiate Dictionary, 1997, pp. 65, 548, 745 and 756, G. &. C. Merriam Co., USA.
Michael P. Henry, Bakerbond Non-Polar Bonded Phases: Hydrolytic Stability, Accessibility of Silanols Re-Equillibrium Times, 1989, 3 pages, www.jtbaker.com.
H. Zhu and M. Snyder, Protein Chip Technology, Curr. Opin. Chem. Biology, 2003, pp. 55-63, vol. 7.
Biljana A. Cavic et al., High Surface Density Immobilization of Oligonucleotide on Silicon, Analyst, 2001, pp. 485-490, vol. 126.

* cited by examiner

*Primary Examiner*—Marc S Zimmer
(74) *Attorney, Agent, or Firm*—Griffin & Szipl, P.C.

(57)     ABSTRACT

The invention relates to sensor chips with multiple layers of polysiloxane with improve homogeneity.

8 Claims, 1 Drawing Sheet

SENSOR CHIPS WITH MULTIPLE LAYERS OF POLYSILOXANE

This is a National Phase Application in the United States of International Patent Application No. PCT/EP01/08545 filed Jul. 24, 2001, which claims priority on European Patent Application No. 00 116 3242.7, filed Jul. 27, 2000.

FIELD OF THE INVENTION

The invention relates to sensor chips with multiple layers of polysiloxane having improved homogeneity.

BACKGROUND OF THE INVENTION

In recent years, there have been developed numerous solid phase systems based on self-assembled monolayers (i.e., SAMs) from bi-functional molecules (i.e., "linkers") that have gained ever more significance in analytical micro technology, wherein specific probe molecules are coupled, or, as the case may be, conjugated, onto the surface of a solid carrier, which can be confirmed with the help of suitable marking (for example, radio active, colored, or fluorescent marking).

For such systems, in analogy to electronic microchips, the term sensor chips has been adopted. In the case of the conjugation of biological molecules (so called "bioconjugation") in such sensor chips, for example, with oligonucleotides or antibodies, one speaks of "Bio Chips." Coupling on the surface of the carrier can be accomplished directly or indirectly. An example of indirect coupling is the coupling of a nucleic acid sequence to be tested by means of hybridisation onto an immobilized, complementary oligonucleotide used as a probe. In this case, the use of the probe has the additional advantage of the natural specificity of the interaction of biological macromolecules.

Typically, for the manufacture of sensor chips, surfaces of metal oxides, or, as the case may be, metalloid oxides, as, for example, aluminumoxide, quartz-glass, glass, are dipped in a solution of bi-functional molecules (so called "linkers"), which comprise, for example, a halosilane-(for example, chlorosilane-) or alkoxy silane group for coupling to the carrier surface so that a self-organized monolayer (SAM) forms. In this case, this SAM comprises a thickness of a few Ångstrom. The coupling of the linkers to the sample or probe molecules takes place by means of suitable further functional groups, for example, an amino or epoxy group. Suitable bi-functional linkers for coupling of a multitude of sample or probe molecules, particularly also those of biological origin, on a multitude of carrier surfaces, are known to one of ordinary skill in the art, see, for example, "Bioconjugate Techniques", GT Hermanson, Academic Press, 1996.

A homogenious and chemically resistant layer can be obtained by this method only with much difficulty. Monofunctional silanes, which are suitable for solid carriers with metal oxide or metalloid oxide surfaces, for example, monochlorosilanes such as aminopropyl monochlorosilane, while they achieve real monolayers, can be split off from the surface merely by means of hot water. Trifunctional silanes, such as, for example, aminopropyltriethoxysilane, form cross-links in solution, which can lead to an inhomogeneous layer of silanes on the carrier surface. Homogeneous layering is not thereby achieved, which results in a loss in quality. In addition, there are also changes in character within a chip series.

A further disadvantage of this process in its practical application is the relatively long incubation time of silane solutions. For an efficient layering, silation times of about two hours are often necessary.

An object of the present invention is, departing from this state of the art, to fabricate a sensor chip with homogeneous layering based on a silane linker, as well as a process which makes such a layer quickly and reproducibly.

SUMMARY OF THE INVENTION

In accordance with the above objects, the present invention provides a sensor chip with a carrier having a surface of metal oxide or metalloid oxide and a homogeneous multiple layer of polysiloxane applied to the carrier surface. The multiple layer of polysiloxane is obtained by a process comprising the steps of (i) immersing the carrier in a solution of bi-functional silane in a solvent with a boiling temperature in the range of from 50-150° C., having a concentration in the range of from 0.1 to 50 weight %, at a temperature of from 20-100° C., and (ii) withdrawing the carrier at a speed in the range of from 0.1 to 10 mm/s, whereby the layer of bi-functional silane is fixed on the surface of the sensor chip by formation of a multiple layer of polysiloxane through cross-linking.

In a further embodiment, the carrier surface of metal oxide or half-metal oxide comprises an $Al_2O_3$- or $SiO_2$-containing surface. In a yet further embodiment the $SiO_2$-containing surface comprises a material selected from the group consisting of (1) glass, (2) quartz glass, (3) a layer of highly dispersed silicon dioxide applied to any solid carrier, and (4) a layer of $SiO_x$ vapour deposited or sputtered on a solid carrier.

In a still further embodiment, the bi-functional silane comprises two or three hydrolysable atoms or groups on a silicon atom.

In yet another embodiment, the hydrolysable atoms or groups are selected from the group consisting of halogen atoms, $C_1$-$C_4$-alkoxy-, $C_1$-$C_4$-acyloxy-, and amino groups. In a still further embodiment, the second functional group of the bi-functional silane is capable of undergoing nucleophilic substitution reactions, nucleophylic addition reactions, Diels-Alder reactions or radical substitution reactions. Another embodiment provides that the second functional group of the bi-functional silane comprises a functional group selected from the group consisting of a reactive double bond, a diene group, a dienophile group, epoxy-, aldehyde-, hydroxy-, carboxylic acid, active ester-, amino-, disulfide-, thiol-, aziridine-, azlactone-, isocyanate-, isothiocyanate-, azide groups and reactive electron donor groups.

In yet another embodiment, the step of immersing further providing a container with a plurality of precisely fit slits for containing a plurality of correspondingly dimensioned carriers. A still further embodiment provides that the precisely fit slits are so dimensioned that the sample carrier can be taken up with its narrow top side. Another embodiment further provides that the slits for take up of the carriers additionally comprises a device for fixing the carrier in the carrier slits. In a still further embodiment, the device for fixing comprises a spring loaded metal ball with which the carriers are pressed into the slits.

In general, the invention rests on the discovery that conventional silane monolayers can be replaced by multiple layers of polysiloxane that can be prepared homogeneously, and, above all, quickly, with known layering methods.

Also, generally, the invention relates to a sensor chip, on whose metal oxide or metalloid oxide surface a homogeneous multiple layer of polysiloxane is put by means of spinning, wiping (application with a wiper blade), spraying, painting (lacquering) or dipping (immersion).

According to a preferred embodiment, such as illustrated in FIG. 1, the above invention relates to a sensor chip 1 with a carrier surface 5 of metal oxide or metalloid oxide, upon which a homogeneous multiple layer 10 of polysiloxane is applied, which is obtainable by immersing the sensor chip in a solution of a bi-functional silane in a solvent having a boiling point in the range of from 50-150° C., with a concentration in the range of from 0.1 to 50 weight % at a temperature of from 20-100° C., and thereafter pulled out again with a speed in the range of from 0.1 to 10 mm/s, whereby a layer with a bi-functional silane is fixed by cross-linking to the surface of the sensor chip by formation of a multiple layer of polysiloxane.

The sensor chips according to the present invention are distinguished by better homogeneity of the multiple layer of polysiloxane as well as better reproducibility and workability. The reproducibility of the sensor properties are thereby also clearly improved. Furthermore, yield is higher and the "aging" of the solution of the bi-functional silanes no longer presents a problem.

A further aspect of the present invention is a device, or, as the case may be, a container, in which a plurality of carriers for later sensor chips can, in parallel, be provided with homogeneous multiple layers of polysiloxane.

Advantageous and/or preferred embodiments of the invention are described below.

Preferred embodiments of the present invention relate to a sensor chip according to the main claim, in which the homogeneous multiple layer of polysiloxane is obtainable, wherein the sensor chip is dipped in a solution of bi-functional silane in a solvent with a boiling temperature in the range of from 50-150° C., preferably 60-90°, for example, ethanol, chloroform, or toluene, with a concentration in the range of from 0.1 to 50 weight %, for example, 0.5 to 40 weight %, preferably 1.0 to 30 weight % or 2 to 25 weight % or 3 to 20 weight % or 5 to 15 weight %, at a temperature of from 20 to 100° C., preferably room temperature, and thereafter withdrawn at a speed in the range of from 0.1 to 10 mm/s, for example, 0.5 to 8 mm/s or 1 to 5 mm/s or to 2 to 3 mm/s.

In this embodiment, neither the immersion depth nor the speed of immersion or the length of immersion plays any role.

Further objects, features and advantages of the present invention will become apparent from the Detailed Description of Preferred Embodiments, which follows.

DETAILED DESCRIPTION OF PREFERRED EMBODIMENTS

Figure 1:
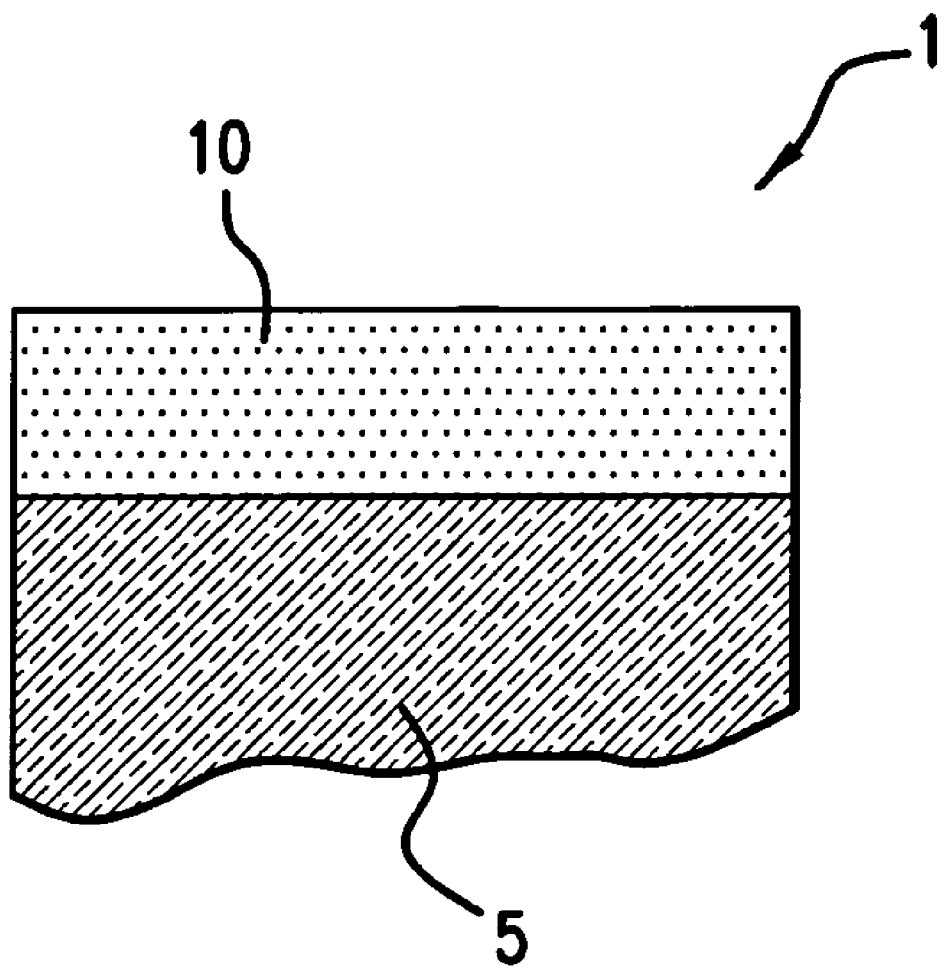
FIG. 1 is a schematic illustrating a preferred embodiment of the invention.

As follows, the invention will be, without limitation, described in further detail with reference to concrete embodiments and examples.

The surface of the sensor chip according the present invention can be made of any desired metal oxide or metalloid oxide or some other carrier that reacts with silane groups to form covalent bonds. For example, these can be $Al_2O_3$- or $SiO_2$-containing surfaces, for example, glass or quartz glass ("fused silica"). An $SiO_2$-containing surface can also be produced, wherein a layer of highly dispersed silicon dioxide ("fumed silica") is applied to a any solid carrier, or layers of $SiO_x$ are vapour deposited or sputtered onto a solid carrier.

The bi-functional silane used is not particularly limited, as long as it can be cross-linked by formation of polysiloxanes. In question are all silanes that have two or three hydrolysable atoms or groups on the silicon atom, for example, halogen atoms, $C_1$-$C_4$-alkoxy-, $C_1$-$C_4$-acyloxy- or amino groups.

The second functional group of the bi-functional silane is also not particularly limited and is selected in accordance with the sample or probe molecule to be immobilized. Examples are reactive groups for nucleophylic substitution reactions, nucleophylic addition reactions, Diels-Alder reactions or radical substitution reactions. Concrete examples are reactive double bonds, diene groups, dienophile groups, epoxy-, aldehyde-, hydroxy-, carboxylic acids, active esters, amino-disulfide-, thiol-, aziridine-, azlactone-, isocyanate-, isothiocyanate-, azide groups and reactive electron doner groups.

Concrete examples are isocyanopropyltrimethoxysilane or glycidoxypropyltrimethoxysilane on a glass carrier.

Immersion layering is possible for homogeneous layering of the surface of a sensor chip with a bi-functional silane, which has for quite some time been applied in the electronic industry for, for example, layering chip wafers or hard drive media quickly with high precision. Other methods, however, are also possible which allow homogeneous layering. For example, layering can take place by spinning, wiping (application with a wiper blade), spraying or painting (lacquering). Immersion layering according to the present invention is particularly preferred, because the layer thickness (in principle any desired thickness, for example, several hundred Angstrom) can be simply regulated by means of concentration of the bi-functional silane, the solvent used, the temperature and the immersion speed. The viscosity of the solution can be adjusted to a suitable value by mixing with pre-polymers as viscosity heighteners, for example, a polydimethylsiloxane with suitable condensable groups, for example, silinol groups, chlorosilogroups, or alkoxysilogroups can be used.

The solvent for the bi-functional silanes is not particularly limited, as long as it is sufficiently quickly vaporized. For example, chloroform, ethanol and toluene are suitable.

The immersion coating of a carrier can take place in five minutes. In comparison, layering by formation of SAMs according to the method of the state of the art takes about two hours.

A further advantage is that immersion layering can take place in with high output in parallel fashion. For example, a simple container for immersion can be utilized in which, for example, 30 conventional sample carriers (the solid phase of the later sensor chips) are, for example, two rows with their narrow top side, or as the case may be handling surface disposed in correspondingly numerous holding slots. These holding slots are fitted to the width (the narrow top side) and the thickness of the sample carrier and can, in addition, be provided with a device for fixing the sample carrier in the holding slot by one or both narrow sides, for example, it can be held with spring loaded metal balls with which the sample carrier is pressed. The immersion depth comprises, for example, 60 mm.

With this carrier, one can, for example, simultaneously immersion coat 30 carriers. The otherwise conventional washing steps are unnecessary and the blowing drying of the carrier is left out.

Since no contact surfaces (outside of the handling surface of the sample carrier) are present, withdrawal can take place without the formation of drops/"noses", which upset the homogeneity of the layering. In this manner, the silation process is not only improved, but also accelerated.

After application, the layer of bi-functional silane with formation of multiple layers of polysiloxine on the surface of the sensor chip is fixed (by cross-linking, for example, by subjecting to air humidity). If necessary, supplemental warming can take place in a drying cabinet with increased air humidity, for example, at 120° C.

The following table shows a comparison between a conventional process and one according to the present invention (silation of 150 sample carriers).

|  | Activating | Silation | Rinsing/Blow Drying | Fixing of the silane layer |
| --- | --- | --- | --- | --- |
| Conventional | 2 hours | 2 hours | 2 hours | 2 hours at 120° C. |
| Invention | Not present | 5 minutes | Not present | 2 hours at 100° C. |

An Exemplary Embodiment Follows:

In the above-described container, 30 glass sample carriers (also later sensor chips) are cleanly inserted with their grip surface (thin upper side) facing upward. The sample carriers were immersed (10 minutes) in a 500 ml hot Hellmanex® solution (detergent solution for cleaning from the Hellma Company) and subsequently rinsed three times for two minutes with a Millapore®) facility with the ionised water and thereafter bathed in ethanol for three minutes. Subsequently, the sample carriers were dried (drying cabinet) or directly dipped in a one-weight % glycidoxy propyltrimethoxysilane solution (toluene solvent). The immersion speed comprised 2.5 mm/s and the withdrawal speed was 0.5 mm/s. After withdrawal, the sample carriers can be directly fixed in a drying cabinet at 120° C.

The invention claimed is:

1. A method of making a sensor chip comprising the steps of:
    (a) providing a carrier disposed in the sensor chip, and having a surface of metal oxide or metalloid oxide; and
    (b) homogenously layering a multiple layer of polysiloxane to the surface of the carrier, wherein the multiple layer of polysiloxane is obtained by a process comprising the steps of:
        i. immersing the carrier in a solution of a single bi-functional silane linker having a concentration in the range of from 0.1 to 50 weight % in an organic solvent, wherein a first functionality of the bi-functional silane linker comprising two or three hydrolysable atoms or groups on a silicon atom enables crosslinking, and wherein a second functionality of the bi-functional silane linker enables immobilization of sample or probe molecules; and
        ii. withdrawing the carrier at a speed in the range of from 0.1 to 10 mm/s, wherein bi-functional silane is fixed on the surface of the sensor chip by formation of a homogeneous multiple layer of polysiloxane through cross-linking, wherein the second functionality of the bi-functional silane linker is capable of undergoing nucleophilic substitution reactions, nucleophilic addition reactions, Diels-Alder reactions or radical substitution reactions.

2. A method as recited in claim 1, wherein the thickness of the multiple layer of polysiloxane is regulated by a speed of withdrawing the carrier.

3. A method as recited in claim 1, wherein silation of the carrier occurs over a period of 5 minutes.

4. A method as recited in claim 3, wherein fixing of the multiple layer of polysiloxane is performed at 100° C. for 2 hours.

5. A method as recited in claim 3, wherein fixing of the multiple layer of polysiloxane is performed at 100° C.-120° C. for 2 hours.

6. A method as recited in claim 1, wherein the solvent has a boiling temperature in the range of from 50-150° C.

7. A sensor chip, comprising:
    (a) a carrier having a surface of metal oxide or metalloid oxide;
    (b) a multiple layer of polysiloxane homogenously layered onto the carrier surface, wherein the multiple layer of polysiloxane is obtained by a process comprising the steps of
        i. immersing the carrier in a solution of a single bi-functional silane linker having a concentration in the range of from 0.1 to 50 weight % in an organic solvent, wherein a first functionality of the bi-functional silane linker comprising two or three hydrolysable atoms or groups on a silicon atom enables crosslinking, and wherein a second functionality of the bi-functional silane linker enables immobilization of sample or probe molecules; and
        ii. withdrawing the carrier at a speed in the range of from 0.1 to 10 mm/s, whereby bi-functional silane is fixed on the surface of the sensor chip by formation of a homogeneous multiple layer of polysiloxane through cross-linking; and
    (c) a sample or probe molecule immobilized by the second functionality of the bi-functional silane linker.

8. A method of making a sensor chip comprising the steps of:
    (a) providing a carrier having a surface of metal oxide or metalloid oxide; and
    (b) homogenously layering a multiple layer of polysiloxane to the surface of the carrier, wherein the multiple layer of polysiloxane is obtained by a process comprising the steps of:
        i. immersing the carrier in a solution of a single bi-functional silane linker having a concentration in the range of from 0.1 to 50 weight % in an organic solvent, wherein a first functionality of the bi-functional silane linker comprising two or three hydrolysable atoms or groups on a silicon atom enables crosslinking, and wherein a second functionality of the bi-functional silane linker enables immobilization of sample or probe molecules; and
        ii. withdrawing the carrier at a speed in the range of from 0.1 to 10 mm/s, wherein bi-functional silane is fixed on the surface of the sensor chip by formation of a homogeneous multiple layer of polysiloxane through cross-linking; and
    (c) immobilizing a sample or probe molecule using the second functionality of the bi-functional silane linker.

* * * * *